United States Patent
Wallace (10) Patent No.: US 8,073,106 B2
(45) Date of Patent: Dec. 6, 2011

(54) ESTIMATING STRENGTHS OF WOODEN SUPPORTS BY DETECTING BACKSCATTERED GAMMA RAYS

(75) Inventor: Gavin Wallace, Wellington (NZ)

(73) Assignee: Institute of Geological and Nuclear Sciences, Wellington (NZ)

( * ) Notice: Subject to any disclaimer, the term of this patent is extended or adjusted under 35 U.S.C. 154(b) by 0 days.

(21) Appl. No.: 12/804,015

(22) Filed: Jul. 12, 2010

(65) Prior Publication Data

US 2010/0316191 A1    Dec. 16, 2010

Related U.S. Application Data

(63) Continuation of application No. 11/899,541, filed on Sep. 6, 2007, now Pat. No. 7,769,131, which is a continuation of application No. PCT/NZ2006/000036, filed on Mar. 6, 2006.

(30) Foreign Application Priority Data

Mar. 7, 2005    (NZ) .................................. 538649

(51) Int. Cl.
*G01B 15/02*    (2006.01)
(52) U.S. Cl. ........................................ 378/89
(58) Field of Classification Search ............... 378/6, 7, 378/54, 58, 86–89
See application file for complete search history.

(56) References Cited

U.S. PATENT DOCUMENTS

| | | | |
|---|---|---|---|
| 3,136,892 | A | 6/1964 | Willett et al. |
| 4,495,518 | A | 1/1985 | Sanoian |
| 4,947,045 | A | 8/1990 | Birks et al. |
| 4,979,197 | A | 12/1990 | Troxler, Sr. et al. |
| 5,021,666 | A | 6/1991 | Reber |
| 5,091,862 | A | 2/1992 | Hoffman et al. |
| 5,099,504 | A | 3/1992 | Pettit |
| 5,105,453 | A | 4/1992 | Hanrahan et al. |
| 5,195,116 | A | 3/1993 | Le Floc'h et al. |
| 5,204,889 | A | 4/1993 | Kraybill |
| 5,418,830 | A | 5/1995 | Florent |
| 5,821,862 | A | 10/1998 | MacKenzie |
| 5,970,116 | A | 10/1999 | Dueholm et al. |
| 6,049,282 | A | 4/2000 | MacKenzie |
| 6,094,470 | A | 7/2000 | Teller |
| 6,252,930 | B1 | 6/2001 | MacKenzie |
| 6,310,936 | B1 | 10/2001 | Troxler et al. |
| 6,320,933 | B1 | 11/2001 | Grodzins et al. |
| 6,442,232 | B2 | 8/2002 | Troxler et al. |
| 6,567,498 | B1 | 5/2003 | Troxler et al. |
| RE38,910 | E | 12/2005 | Troxler et al. |
| 2002/0080914 | A1 | 6/2002 | West et al. |
| 2004/0057551 | A1 | 3/2004 | Skatter et al. |

FOREIGN PATENT DOCUMENTS

| | | |
|---|---|---|
| WO | WO 88/07671 | 10/1988 |
| WO | WO 91/05245 | 4/1991 |
| WO | WO 00/52454 | 9/2000 |

*Primary Examiner* — Irakli Kiknadze
(74) *Attorney, Agent, or Firm* — Thomas R. Vigil (57) ABSTRACT

A method of estimating the strength of a wooden support wherein gamma rays (4) are transmitted and detected parallel to a neutral axis (5) through a cross section of the support. It also includes a method of locating regions of unsound wood in a wooden support using detection of transmitted gamma rays (4), as well as apparatus suitable for conducting both methods.

11 Claims, 12 Drawing Sheets

ESTIMATING STRENGTHS OF WOODEN SUPPORTS BY DETECTING BACKSCATTERED GAMMA RAYS

CROSS REFERENCE TO RELATED APPLICATIONS

This application of PCT/NZ2006/000036, filed Mar. 6, 2006, which claims priority from New Zealand Applicaton No. 538,649, filed Mar. 7, 2005.

FIELD OF INVENTION

The invention relates to a system and method for estimating the strengths of wooden supports.

BACKGROUND

Wooden supports have many applications including supporting power lines, bridges, wharves, and buildings. The wooden supports are selected for use based on the load anticipated on the support. The size of the support, timber species, and treatment of the support are all important selection factors. While in service the supports may degrade and weaken due to a number of causes such as termite infestation and fungus attack. The deterioration of the wooden supports may be entirely internal and not visible on the outside of the support. Degradation in wooden supports is often unpredictable and the onset of loss of integrity in the support may not be related to time in service. Further to this some internal defects leave the wooden supports with sufficient strength that replacement of the support is unwarranted and wasteful. It is therefore desirable to provide a system and method that can assess the strength of the wooden support.

Current industry 'best practice' for determining deterioration in a wooden pole or support is to periodically drill into the wooden support to determine the annulus of the remaining sound wood. An average wall thickness for the wood support is then assumed. This method produces a high level of uncertainty due to both the variability of wood strength and the inherent errors in determining section properties. Further to this, drilling and plugging holes in wooden supports is undesirable.

Another device for measuring the extent of decay in a wooden support is an inspection probe that is inserted into an inspection hole drilled in a wooden support. One end of the probe includes a barb that engages with the side wall of the inspection hole and shears fibres from the inspection hole as the probe is withdrawn. The mechanical force needed to withdraw the probe from the inspection hole is measured with a pull-force over a certain value indicating a transition within the wooden support from decaying wood to sound wood. This device suffers from the same hole drilling and plugging problem as the current best practice described above.

A non-destructive method of estimating the residual strength of wooden supports uses portable computed tomography to image cross sections of the wooden supports. This method involves taking a plurality of gamma or x-ray attenuation measurements of the wooden support at varying locations around a 180 degree section of the wooden support. The attenuation measurements are then combined to provide a density image of the wooden support from which a strength estimate can be made. This method is reliable but is time consuming to take measurements with each wooden support measurement taking between ten and fifteen minutes.

SUMMARY OF INVENTION

In broad terms in one aspect the invention comprises a method of estimating the strength of a wooden support comprising the steps of transmitting gamma rays parallel to a neutral axis through a cross section of the wooden support, detecting the gamma rays transmitted through the wooden support, determining the average density of the gamma rays in rows parallel to the neutral axis, assessing the amount of unsound wood in each row, and calculating the strength of the wooden support.

Preferably the method comprises making two cross section measurements at different points on the wooden support, one measurement being a reference measurement taken through wood that is assumed to be sound and the other measurement taken through wood to be analysed.

In one embodiment the wooden support is partially buried, and the wood to be analysed is near or below ground level.

In one embodiment the gamma rays are transmitted by a single gamma ray source, and are detected by a single gamma ray detector. In an alternative embodiment the gamma rays are transmitted by a plurality of gamma ray sources, and are detected by a plurality of gamma ray detectors.

In broad terms in one aspect the invention comprises a method of locating regions of unsound wood in a wooden support comprising the steps of:
a) estimating the strength of the wooden support by transmitting gamma rays parallel to a neutral axis through a cross section of the wooden support, detecting the gamma rays transmitted through the wooden support, determining the average density of the gamma rays in rows parallel to the neutral axis, assessing the amount of unsound wood in each row, and calculating the strength of the wooden support,
and conducting either one or both of steps b) and c):
b) (either before or after step a), determining the density of sound wood of the wooden support, directing gamma rays approximately normal into the surface of the wooden support, detecting the gamma rays that are backscattered approximately 180 degrees, comparing the measured rates with those of the sound timber to estimate the thickness of wood.
c) repeating step a) but in rows substantially orthogonal to the neutral axis.

Preferably both steps b) and c) are carried out.

Preferably step b) is carried out in a plurality of locations over the surface of the wooden support.

In one embodiment the density of the sound wood is determined as a result of carrying out step a). Preferably the backscatter rate from sound wood is calculated using pre-calibration.

In an alternative embodiment the density of the sound wood is determined by directing gamma rays approximately normal into the surface of the wooden support in a region where there is at least 150 mm of sound wood, detecting the gamma rays that are backscattered approximately 180 degrees, and calculating the density.

In broad terms in one aspect the invention comprises a device for estimating the strength of a wooden support and/or for locating regions of unsound wood in a wooden support comprising a frame adapted to be positioned around the wooden support, at least one gamma ray source and at least one gamma ray detector, the gamma ray source and detector positioned on the frame to transmit and detect gamma rays through a wooden support parallel to a neutral axis of the wooden support, computation means arranged to receive a signal from the at least one detector, determine the average density of the gamma rays in rows parallel to a neutral axis, assess the amount of unsound wood in each row, and calculate the strength of the wooden support.

In one embodiment the device is provided with one gamma ray source and one gamma ray detector arranged so that the gamma ray source and detector are moveable in a direction perpendicular to the neutral axis of the wooden support. In an alternative embodiment the device is provided with a plurality of gamma ray sources and a plurality of gamma ray detectors spaced substantially perpendicular to the neutral axis of the wooden support.

In one embodiment the gamma ray source(s) and gamma ray detectors(s) may be repositioned so that only those gamma rays that are backscattered off atomic electrons through an angle close to 180 degrees are detected by the gamma ray detector(s).

In one embodiment the device may include a transmitter or a memory device to store data produced by the gamma ray detector(s) in response to detected gamma rays.

In one embodiment the device may include a GPS unit.

In broad terms in one aspect the invention comprises a method of estimating the strength of a wooden support substantially as herein described with reference to the Figures and/or Examples.

In broad terms in one aspect the invention comprises a method of locating regions of unsound wood in a wooden support substantially as herein described with reference to the Figures and/or Examples.

In broad terms in one aspect the invention comprises a device for estimating the strength of a wooden support and/or for locating regions of unsound wood in a wooden support substantially as herein described with reference to the Figures and/or Examples.

As used herein the term "and/or" means "and" or "or", or both.

As used herein "(s)" following a noun means the plural and/or singular forms of the noun.

The term "comprising" as used in this specification means "consisting at least in part of", that is to say when interpreting independent paragraphs including that term, the features prefaced by that term in each paragraph will need to be present but other features can also be present.

Where, in the specification we refer to "strength" of a wooden support we mean the ability to withstand applied forces, and is represented by the available bending moment of the structure about a neutral axis.

Where, in the specification we refer to "sound" in terms of wood, we mean wood that has not suffered any degradation due to decay, fungal or termite attack, or any other form of material deterioration that reduces the strength of the structure.

Where, in the specification we refer to "critical area" or "critical zone" we mean the area or zone of which the support may break if sufficient decay or deterioration occurs.

It should also be noted that gamma rays are considered to be the same as x-rays and either a gamma ray or an x-ray source may be provided in the gamma ray device.

To those skilled in the art to which the invention relates, many changes in construction and widely differing embodiments and applications of the invention will suggest themselves without departing from the scope of the invention as defined in the appended claims. The disclosures and the descriptions herein are purely illustrative and are not intended to be in any sense limiting.

Other aspects of the invention may become apparent from the following description which is given by way of example only and with reference to the accompanying drawings.

BRIEF DESCRIPTION OF DRAWINGS

The invention will be further described by way of example only and without intending to be limiting with reference to the following drawings, wherein.

DETAILED DESCRIPTION

A wooden support may be a power pole, bridge support, wharf support, a building support or any other support member. While in service these supports are subject to forces. For example a power pole supports overhead line(s) and is subject to forces such as wind loading. The bending moment applied to the pole, $M_R$, is the load times the height at which it is applied. The available bending moment, $M_A$, of the pole must exceed the bending moment applied to the pole, otherwise the pole is likely to break at ground level ('the critical area'). The available bending moment, $M_A$, at any particular section of the pole can be readily calculated if there is detailed knowledge of the distribution of good wood within the cross section. The available bending movement is defined as:

$$M_A = ZF_m$$

where $F_m$ is the ultimate extreme fibre stress of the timber (also referred to as the modulus of rupture, typically 70-100 MPa for Australian hardwoods), and Z is the critical section modulus of the pole. The critical section modulus is defined as $$Z = \frac{I}{s}$$

Where, I is the moment of inertia of the section in relation to a defined neutral axis, and is the distance in the direction of the critical load of the furtherest good wood under tension from the critical load.

Figure 1:
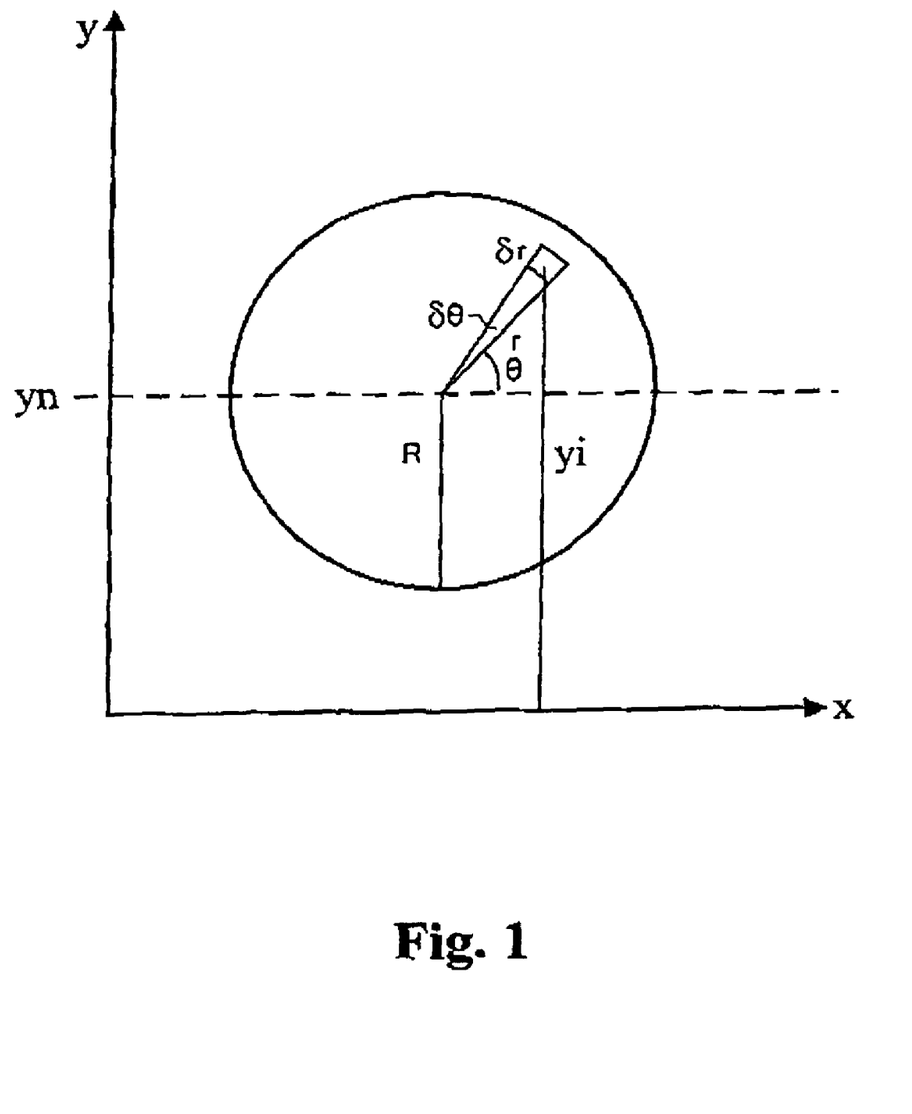
FIG. 1 shows the calculation of the moment of inertia about a neutral axis.

FIG. 1 is a diagram of a pole with circular cross section of radius R. The neutral axis, $y_n$, is an axis along which stress and strain are zero. If there are no internal defects in the wooden support then the moment of inertia is, $$I = \int_0^{2\pi} \int_0^R r \, d\theta \, dr (r \sin\theta)^2 = \frac{\pi R^4}{4}$$

from which the critical cross section of a circular wooden support is $$Z_c = \frac{I}{R} = \pi \frac{R^3}{4}$$

With irregularly-shaped cross sections or square poles, section moduli can be digitally calculated from photographs or other images of the cross sections. If the image is composed of pixels (i,j) of side w, and the neutral axis is defined as $y=y_n$ calculation for the moment of inertia becomes $$I = w^2 \sum_i \sum_j (y_{ij} - y_n)^2$$

and $$Z = \frac{I_o}{\max|y_{ij} - y_n|}$$

The use of the attenuation of a gamma ray or x-ray beam through an object is a standard technique to determine either the thickness of the object, if the object is uniform in density, or the average density of the object if the thickness is known. A beam of gamma rays passed through an object will be attenuated exponentially:

$$\Psi = \Psi_o e^{-\mu \rho t}$$

where $\psi_o$, is the incident beam intensity, $\psi$ is the transmitted beam intensity, t is the thickness of the absorbing object, $\mu$ is the mass absorption coefficient of the absorbing object at the energy of the gamma rays, and $\rho$ is the density of the absorbing object. An irregularly shaped object, or one with absent internal material, can be represented as an array of pixels, side w, with densities $\rho_i$:

$$\sum_j \rho_{ij} = -\frac{1}{\mu w} \ln\left(\frac{\Psi}{\Psi_o}\right)$$

It is assumed that the mass absorption coefficient $\mu$ is independent of the pixel density. If a circular image is Nw in diameter, $\pi N^2/4$ measurements are required to evaluate the image. Using computed tomography thousands of attenuation measurements ('ray sums') can be made and grouped in projections to evaluate individual $\rho_{ij}$. CT images are essentially digital maps of density. In terms of estimating section moduli, density maps are a means to an end. A simpler method based on far fewer measurements would have much merit if similar accuracy can be achieved.

For a power pole the major load is transverse to the overhead transmission line. The major load is primarily the section modulus about a neutral axis parallel to the line that is of most importance when gauging a pole for continued serviceability. Furthermore, the centres of poles contribute little to the strength. Support for these views can often be seen in the design of concrete power poles. Round poles are usually hollow; non-round poles may have 'I' beam cross sections, or may be composed of two rectangular beams joined at intervals along the pole. These shapes of non-wooden supports imply that a wooden support that is decayed in the centre may not need replacement.

Figure 2A:
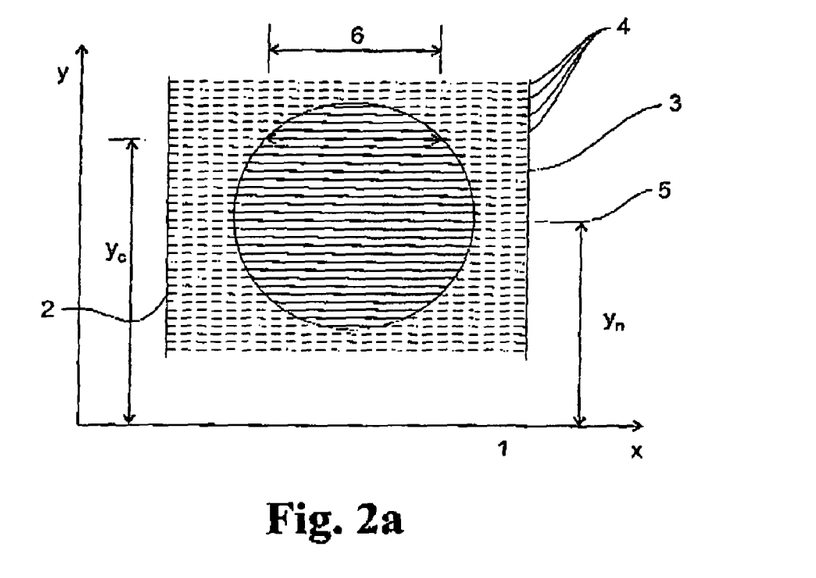
FIG. 2A shows measurement on a cross section of a wooden support.

FIG. 2A shows a series of gamma rays 4 traversing a wooden support 1 with a substantially circular cross section. The gamma rays begin at source line 2 and are detected along detector line 3. Axis 5 represents the neutral axis.

It should be noted that 'chord' in the description means a straight line segment connecting two points on a surface and lying between them. Although the word chord is usually used when referring to circles it can also be used for any curve or surface. Use of the word chord in this specification extends to non-circular cross sections of wooden supports.

Taking a series of ray sums parallel to the neutral axis $y_n$, (5 in FIG. 2A), effectively gives a density profile in they direction. If the cross section of the pole is assumed to be circular or elliptic (as shown in FIG. 2A), then the number of pixels $N_i$ traversed by the ray at that distance ($y_i-y_n$) can be calculated; it is just the estimated length of that chord 6 divided by the pixel size, w. However, because it is the integral attenuation that is measured, only the average density $\rho_i$ of those pixels in the chord can be found. This approach can also be used for supports with a square or rectangular cross section. For these wooden supports the number of pixels traversed by a gamma ray at distance ($y_i-y_n$) will be the same regardless of the location on the support. The average density of these pixels can then be found. It should be noted that the word pixel is used to define an element of area. Each pixel is square. The pixel size is equal to the width of the gamma rays passing through the wooden support. The smaller the width of the gamma rays passing through the wooden support the smaller the pixel size w.

The average density of the $N_i$ pixels traversed by the gamma ray at distance ($y_i-y_n$) is $$\rho_i = \frac{1}{N_i} \sum_j \rho_{ij} = -\frac{1}{\mu w N_i} \ln\left(\frac{\Psi}{\Psi_o}\right)$$

Assuming that the wood is of density $\rho$, and that the chord density $\rho_i$ is lowered because of missing wood ($\rho=0$), then only $N_i' = N_i \rho_i/\rho$ of the chord pixels are effective. Unlike full imaging, it is not necessary to identify individual defective pixels as they are all at $$I = w^2 \sum_i N_i'(y_i - y_n)^2$$

the same distance from the neutral axis. The reduced moment of inertia is then and the critical section modulus of the wooden support is $$Z = \frac{I}{\max|y_i - y_n|} \text{ for } \rho_i > 0$$

As shown in FIG. 2A a plurality of substantially parallel rays are used to scan a cross section of the wooden support. Scanning a cross section of the wooden support may be achieved by using a plurality of gamma ray sources and detectors or by using one gamma ray source and one gamma ray detector that moved along lines 2 and 3 to produce and detect the plurality of substantially parallel gamma rays. The number of substantially parallel gamma rays per wooden support may be varied. In this specification this is shown by the pixel size. The smaller the pixel size the greater the number of substantially parallel gamma rays per wooden support.

Figure 2B:
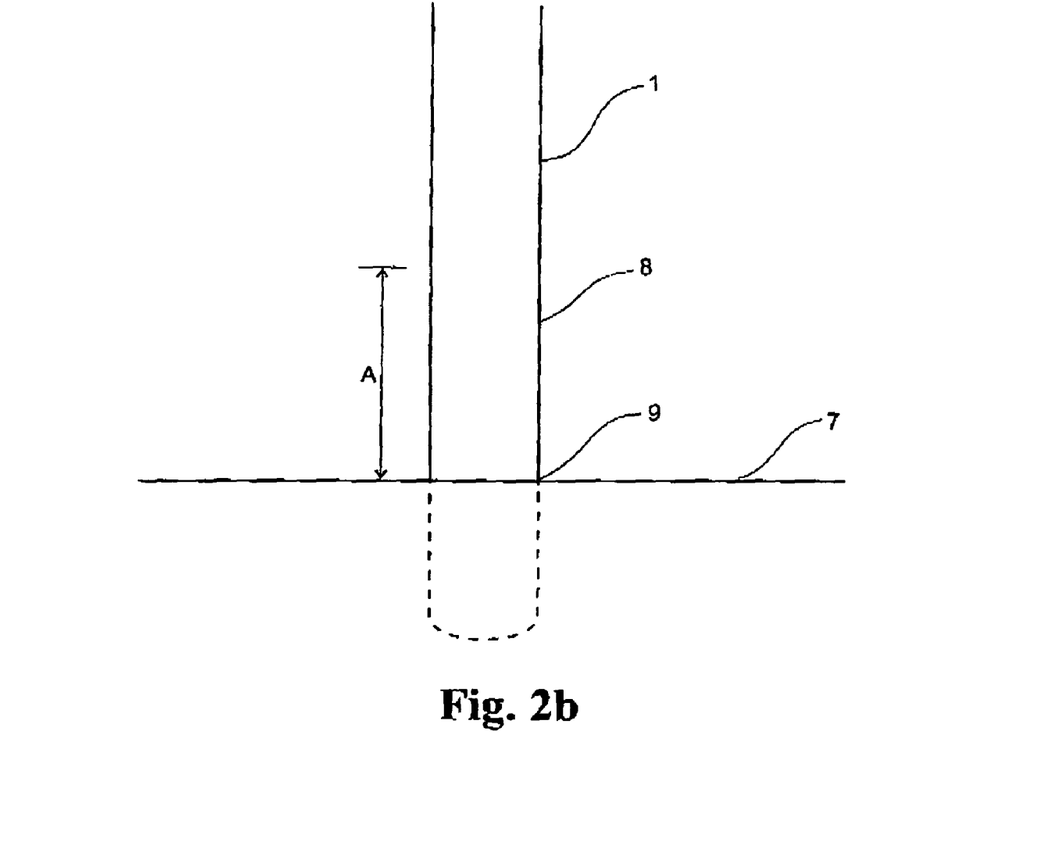
FIG. 2B shows the points of measurement on a wooden support.

FIG. 2B shows a wooden support 1 that is partially buried. As previously discussed for partially buried wooden supports the critical area is near ground level 9. The critical area is the area at which the support may break if sufficient decay or deterioration occurs. As each wooden support may have a different density from surrounding wooden supports a reference measure may be taken on the wooden support. In the embodiment shown in FIG. 2B the reference measurement takes place at point 8 which is height A above ground level. For power poles a reference measure may typically be taken 1-2 m above ground level. The strength measurement takes place in the critical area of the wooden support. If the strength measurement is taken below ground level some excavation around the support will be required.

Figure 3:
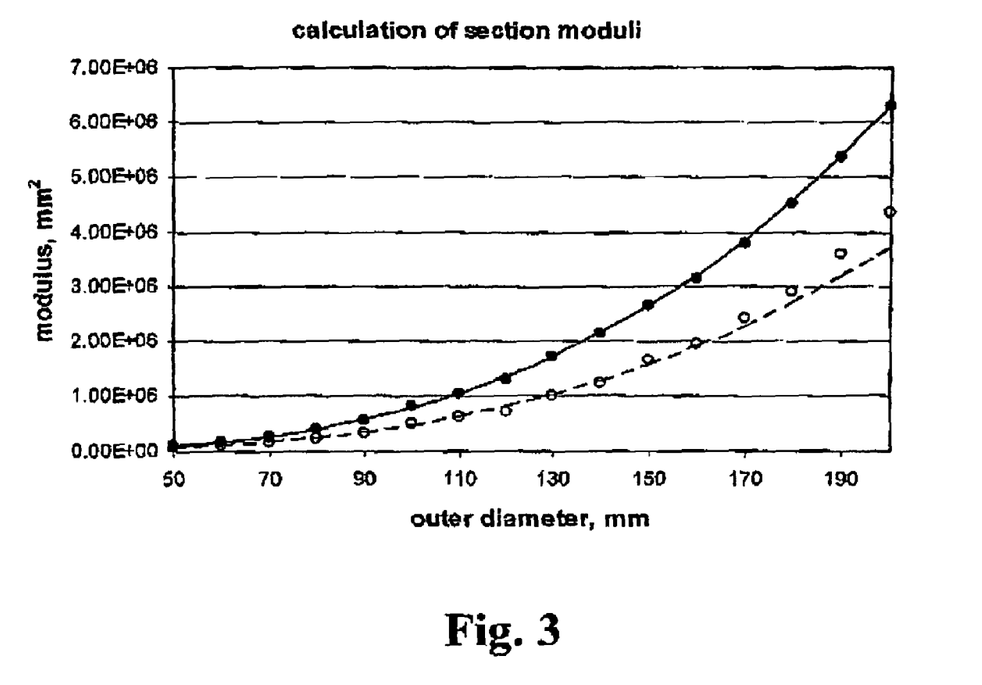
FIG. 3 is a graph showing the calculation of section moduli about a neutral axis.

FIG. 3 shows a comparison of this numerical procedure with analytic calculations for sound poles and for poles with internal holes of diameters 80% of external diameters. In FIG. 3 the lines are the section moduli calculated using the circle formula and the points are numerical chord analysis. The solid lines and points represent the wooden supports with solid cross sections and the broken lines and open points represent cross sections for wooden supports with internal holes of 80% of the external diameter. The outer diameter of the wooden support is shown along the X axis of this Figure. FIG. 3 shows that the section moduli become increasingly less accurate for wooden supports with larger diameters. A tendency to over-estimate values can be seen in the points for the numerical chord analysis. Over-estimating values is probably the result of the pixel size used in the scans when the walls are very thin. For some of the supports the walls are down to about three pixels thick. In the case of a 400 diameter wooden support, the residual wall thickness is 40 mm and the strength becomes that of a 315 diameter wooden support. FIG. 3 shows that the current invention provides a section modulus measurement of reasonable accuracy for wooden supports.

In use in the present invention the density of pixels in line with the end points defined by the gamma ray source and detector are determined. If the length of the chord of the wooden support at the point between the gamma ray source and detector is known, then the average pixel density along the chord can be calculated. If the average is less than the timber density of the pole, it can then be assumed that internal degradation has caused this loss of density and that some of the chord pixels are not contributing to the section modulus. The location of the degraded pixels within the chord is irrelevant when calculating a section modulus for the wooden support. Two assumptions that are used here are that the density of degraded pixels can be set to zero to estimate the number of strengths contributing pixels, and that non-circular or elliptical wooden supports do not have a significant influence on results when a circular cross section is assumed.

Figure 4A:
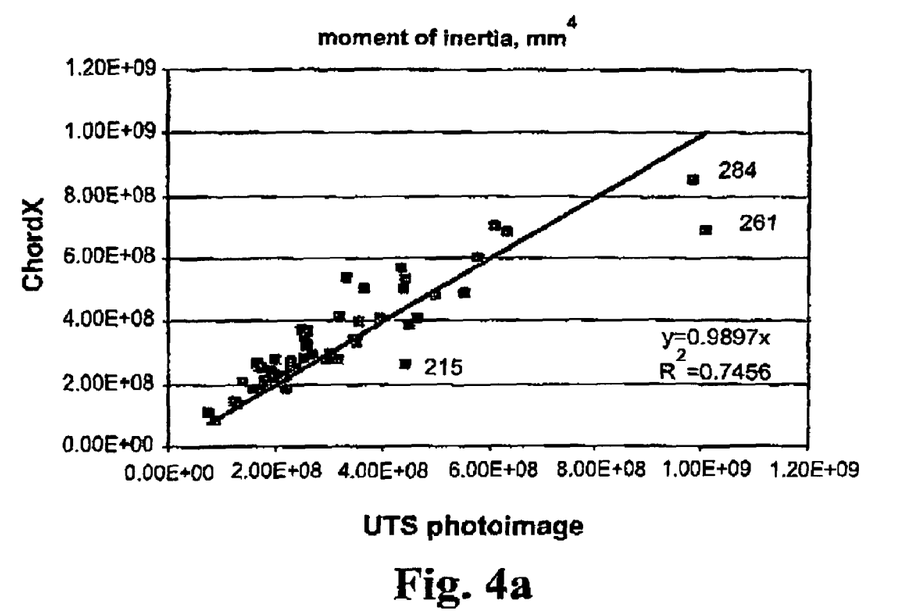
FIG. 4A is a graph showing the comparison of calculations of the moment of inertia using the current method and system of the invention with photo image analysis for a plurality of wooden supports.
Figure 4B:
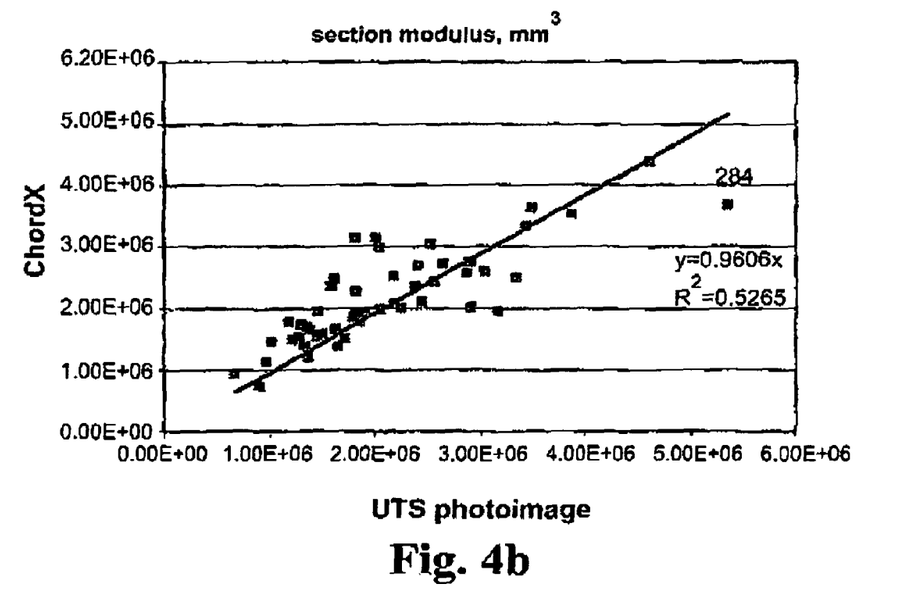
FIG. 4B is a graph showing the comparison of calculations of the section modulus using the current method and system of the invention with photo image analysis for a plurality of wooden supports.

FIGS. 4A and 4B are graphs showing the moment of inertia and section modulus respectively for a number of poles as determined by the present invention and from a photo image analysis. These Figures show that there is very good agreement between the results achieved by the present invention and those of the photo image analysis. Outlier 261 is a solid pole of non-circular cross section and outlier 284 is a hollow pole which also has a non-circular cross section. It should also be noted that the images for outlier 215 were at slight angles to each producing the error seen for this support.

Figure 5:
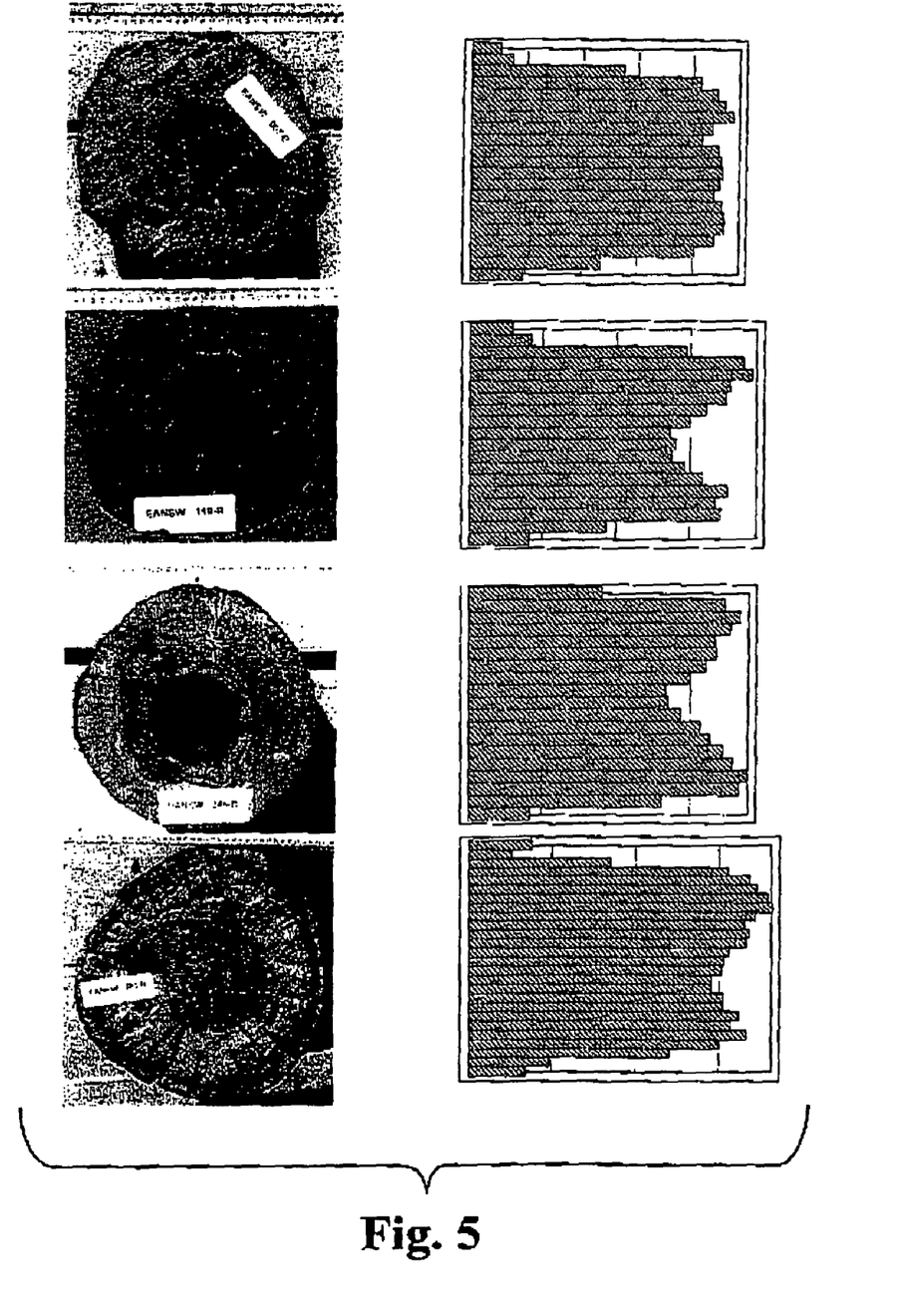
FIG. 5 shows examples of photo images for a number of wooden supports, density images formed using a different method, and density values from the current invention.

FIG. 5 shows the photo images for a number of poles and the density profiles produced by the current invention. The first pole is substantially solid and the density of the pole is reflected in the shape of the density profile produced by the current invention. The second pole includes a small hollow core and the effect of the hollow core is shown in the dip in the centre of the density profile produced by the current invention. The third wooden support has a hollow core and the effect of the hollow core is shown by the dip in the density profile provided by the current invention. The final pole has a rotten core and is also substantially non-circular. The density profile produced by the present invention illustrates the drop in density produced by the rotten core and credits this pole with lower section moduli than estimated visually.

Figure 6:
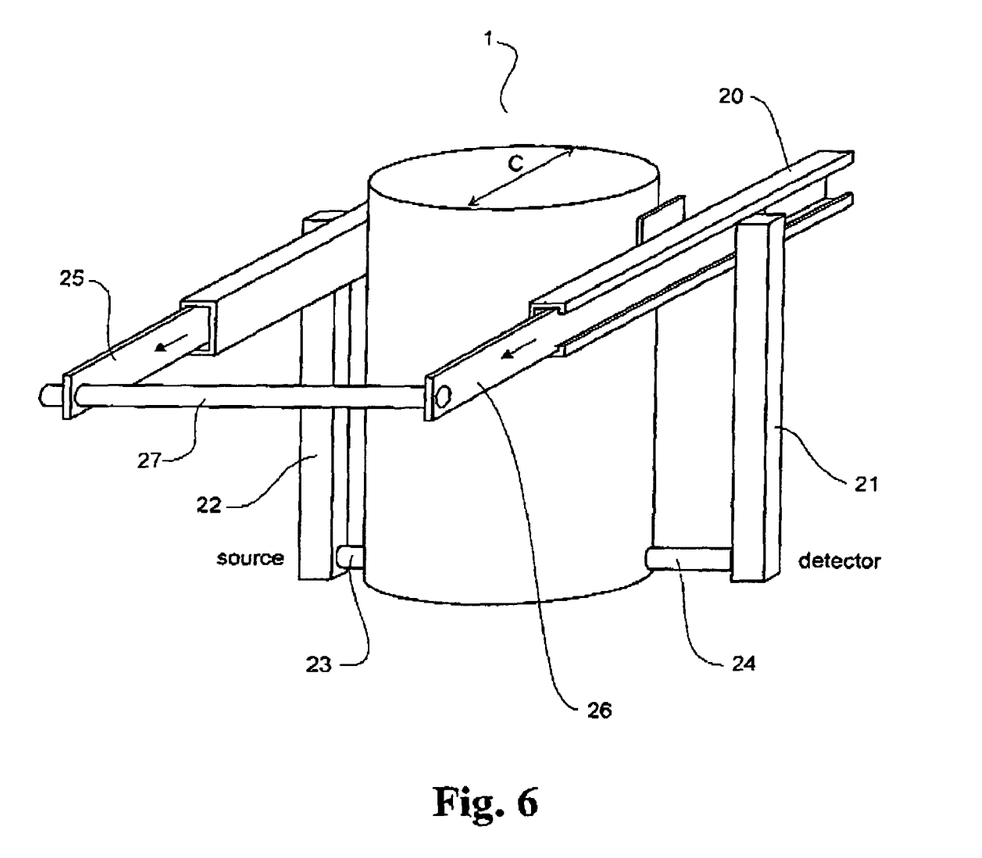
FIG. 6 shows an example configuration for the implementation of the system of the invention.

FIG. 6 shows one possible embodiment of strength detector for wooden supports of the invention. The apparatus for measuring strength of wooden supports includes a frame 20 that is adapted to clamp to the wooden support. Frame 20 includes downwardly extending supports 21, 22. A gamma ray source 23 and detector 24 are attached to supports 21 and 22 respectively. Downward supports 21 and 22 are attached to positioning arms 25 and 26. Positioning arms 25 and 26 are arranged to move backwards and forwards along the direction of arrow B. To ensure rigidity of the frame support 27 extends between arms 25 and 26 to correctly space those arms. In preferred embodiments the length of support 27 between arms 25 and 26 can be adjusted so that the apparatus can fit around wooden supports of varying cross sections.

It should be noted that FIG. 6 shows only one embodiment and possible configuration of the strength detector of the invention. In this embodiment only a single gamma ray source and single detector are used to take multiple measurements along substantially parallel chords across the wooden support as the positioning arms 25 and 26 are moved in the direction of arrow B. In alternative embodiments more than one source and more than one detector may be used. In further alternative embodiments different means may be provided to either move the sources and detectors or to arrange the sources and detectors around the wooden support. The important feature is that the source(s) and detector(s) are arranged so that a plurality of substantially parallel measurements is made through the wooden support. The device shown in FIG. 6 with a single source and a single detector may include motor means for automatically moving the source and detector to scan the wooden support.

Furthermore it should be noted that in certain situations it will be desirable to conduct further measurements orthogonally to the original measurements. Such an orthogonal scan, when compared with the original, can give further details about the location of holes or cavities inside the wooden support which have been observed in cross section. This will not be possible in some cases (such as for bridge supports) as you may not have access to the rear or all surfaces of this support.

As shown in FIG. 6 downward supports 21 and 22 allow a scan of the cross section of a wooden support below ground level with excavation of material around the wooden support for the downward supports, the source and the detector. In this embodiment support arms 25 and 26 remain above ground level. In alternative embodiments the arrangement of the gamma ray source(s) and detector(s) with the frame may be different. For example in some embodiments downward supports 21 and 22 may not be present. In these embodiments the gamma ray source(s) and detector(s) may be connected directly to positioning arms 25 and 26.

The gamma ray source may be any suitable source of gamma rays. For example an Am-241 radio isotopic source may be used. This source produces 60 keV gamma rays. In alternative embodiments any suitable gamma ray source can be used. The gamma rays are tightly collimated within the source so that no stray rays are emitted.

In preferred embodiments the apparatus includes a transmitter or a memory device to store data produced by the gamma ray detector in response to detected gamma rays. This data can either be stored on the apparatus and later downloaded or can be transmitted by a wired or wireless means to a memory source. For example a PDA could be used to store the results.

In another embodiment a GPS unit could be attached to the apparatus or to a connected memory device. The GPS unit provides location information for each of the wooden supports. Use of a GPS device, or other location information, will allow the strength measurement results for the wooden supports to be stored, searchable, and indexable so that a history of results for a particular wooden support could be provided. Over time a picture of deterioration could be provided for each support after numerous scans. It is possible the scan deterioration information could be used to predict when a support will need replacement.

As well as detecting gamma rays through the wooden support the apparatus may be adapted to measure the diameter of the wooden support under scan. For example a measurement could be provided using a single gamma ray source and detector that had moved along the wooden support as shown in FIG. 6. In this embodiment before the wooden support is encountered by the source and detector there will be a large flux of gamma rays detected by the detector. Once the wooden support is encountered this will drop sharply as the wooden support attenuates gamma rays for resource. Once the source and detector move past the other end of the wooden support the flux of gamma rays detected by the detector will rapidly increase as there will be no attenuation from the support. The distance between these two events as determined by the movement of the source and detector along the support can be used to determine a diameter or length measurement along the wooden support in direction C as shown on FIG. 6. If it is then assumed that the wooden support is circular this measurement gives a maximum diameter in the X axis or direction of the gamma rays. If it is assumed that the wooden support is square then the measurement gives the length measurement of the wooden support in both directions. Alternatively, other means could be used for determining the approximate diameter, length, or width of the wooden support. For example a light source and a photo diode could be used instead. A further alternative would be to measure the circumference of the wooden support and an assessment could be made as to the shape of the wooden support. The assessment could be an assessment as to whether the wooden support is square, rectangular, circular or elliptical. If the wooden support is square or circular then the calculation of the maximum width of the support cross section is easy to obtain. If the support is rectangular the width of the support can easily be measured. For an elliptical support, if the circumference is known, and either the major or minor axis is known through a separate measurement the other axis can then be measured and the cross section of the wooden support can be determined.

In another embodiment, the source(s) and detector(s) may be mounted to function as a backscatter probe to estimate the residual wall thickness arising from the presence of an internal hole within the wooden structure. While the transmission mode of the preferred embodiment accurately determines the section modulus, a single scan cannot determine either the shape or location of the hole within timber cross section.

Figure 7:
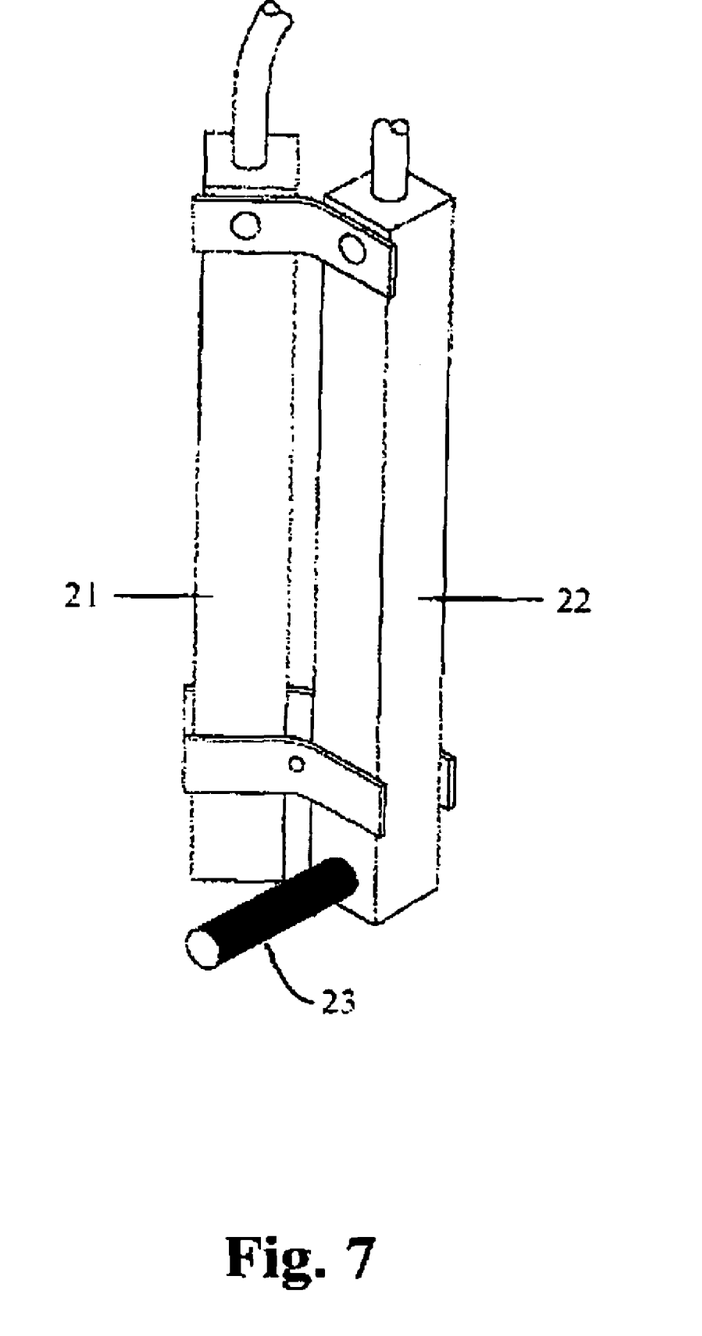
FIG. 7 shows an example configuration for the implementation of the backscatter measurements on the invention.
Figure 9:
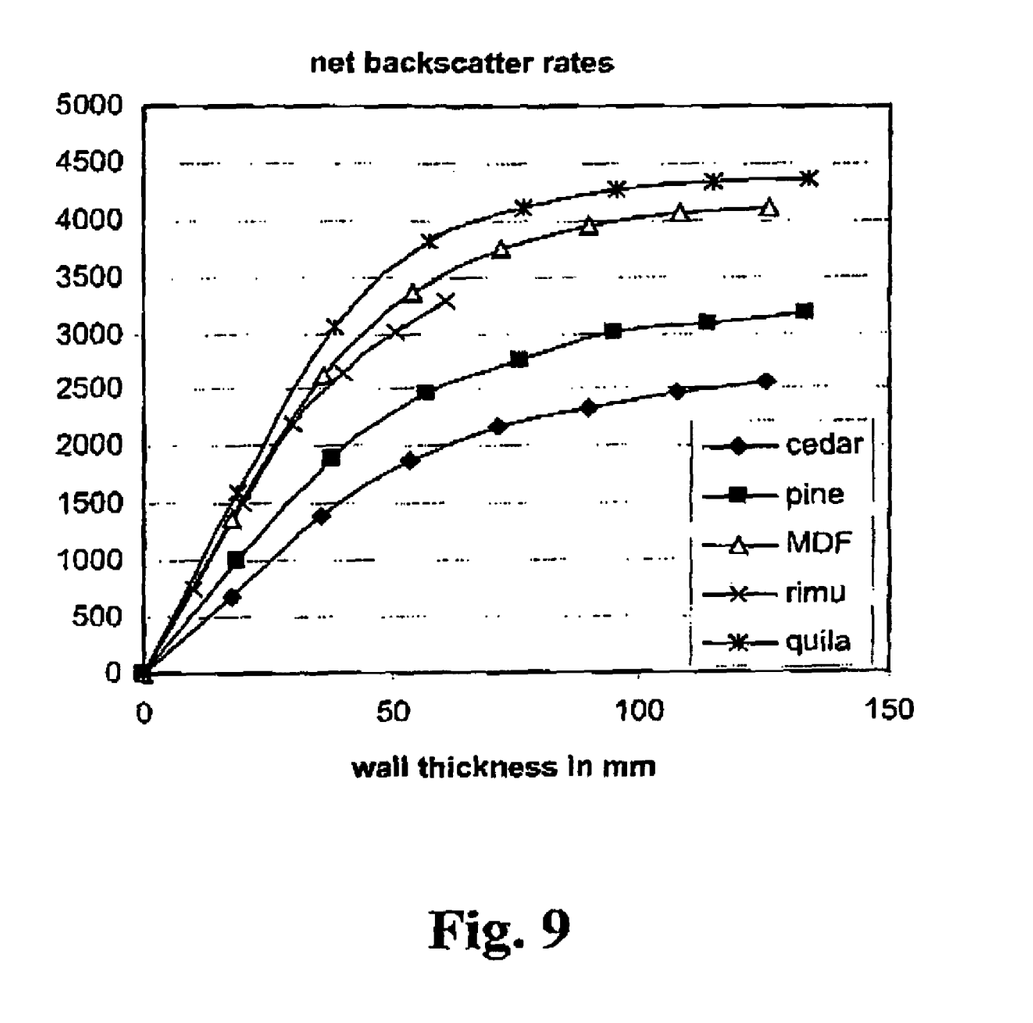
FIG. 9 is a graph relating wall thickness to backscatter rates.

The backscatter probe is formed by using accessory attachments so that downward supports 21 and 22 are parallel, and attached, such that the emitted gamma rays 23 are directed away from the detector as illustrated in FIG. 7. This non-transmission mode is a backscatter mode of detection, and only those gamma rays that are Compton-scattered off atomic electrons through an angle close to 180 degrees can be detected. It is well known that for low atomic number scatterers, such as timber, the detected scatter rate is directly proportional to the density of the scatterer. However, if the scattering material is of less than infinite depth, the detected rate will also vary with the thickness of the material. These combined effects are shown in FIG. 9. The named timbers in this figure range in density from 350 to 880 kg/m$^3$. If the density of the scattering material is known, then its thickness, up to about 100 mm, can be estimated from the measured scatter rate of detection.

Figure 8:
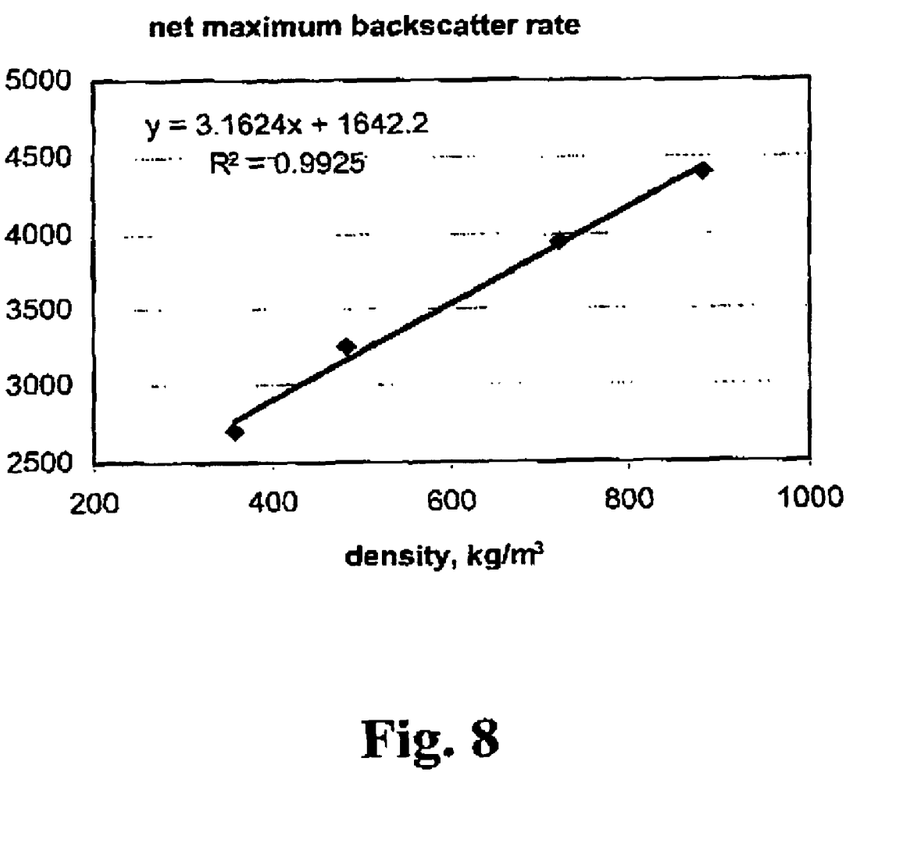
FIG. 8 is a graph relating density to net maximum backscatter rate.

This backscatter embodiment may therefore be combined with the preferred transmission embodiment. A sound wood density is required in order to carry it out. In one case once the transmission methodology has been used to scan a wooden support, a sound wood density value has been established and this can be used. Alternatively, detection of the backscatter rate from a sound part of the support can be used to measure this density, as shown in FIG. 8. Backscatter rates from the surface of suspect sections of the support can then be used to estimate the wall thickness that remains following internal degradation of the timber.

In practice the backscatter methodology is only used when internal degradation is suspected. The transmission measurement will detect internal degradation, but will not determine its precise location within the cross sectional image. Backscatter could be used to check that the degradation is sufficiently below the surface not to be a problem.

Figure 10:
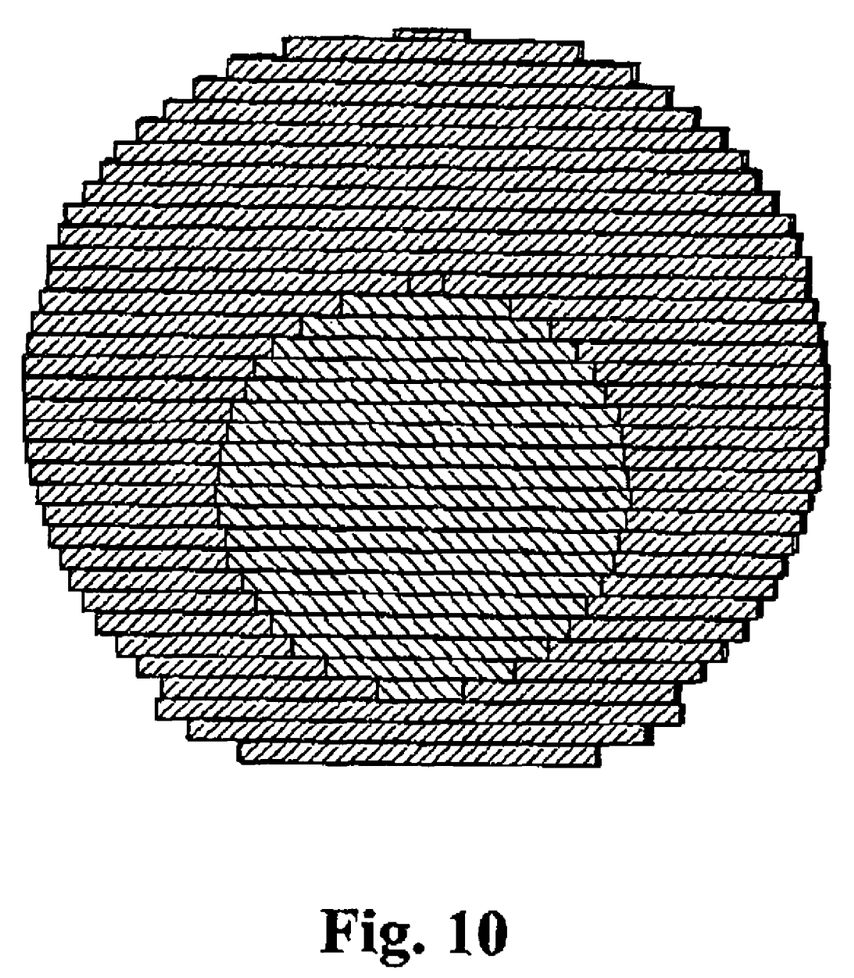
FIG. 10 is a profile of a wooden support following transmission investigations.
Figure 11:
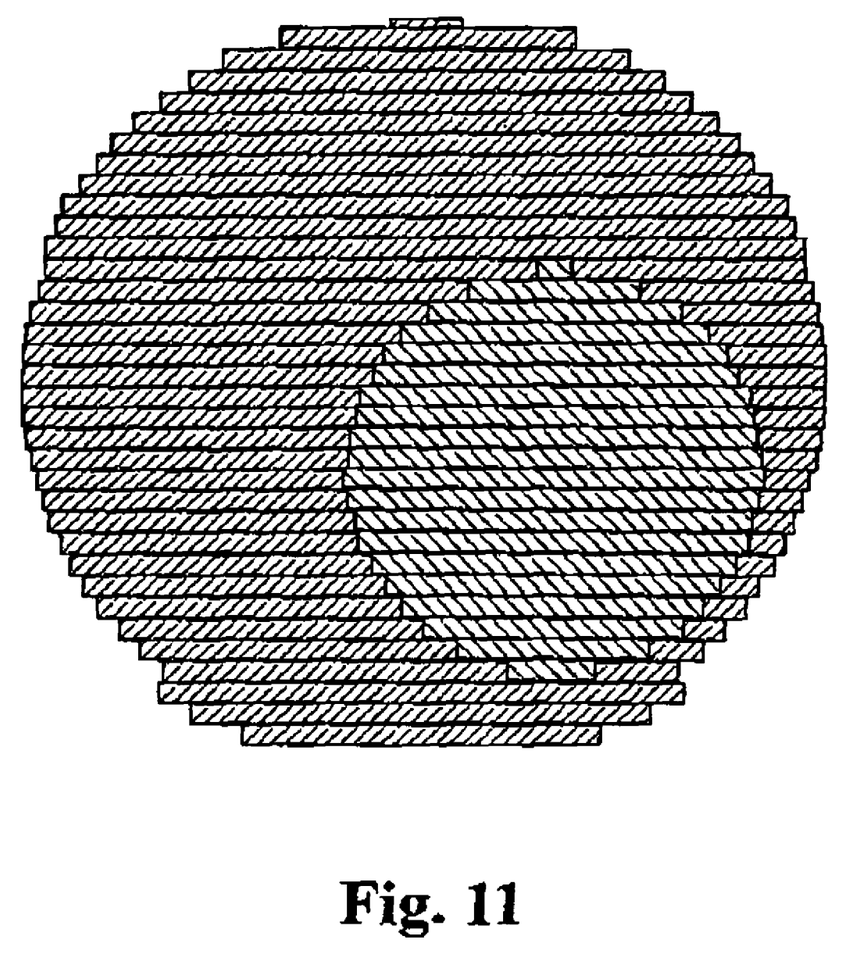
FIG. 11 is the profile of FIG. 10 with superimposed orthogonal scan results.
Figure 12:
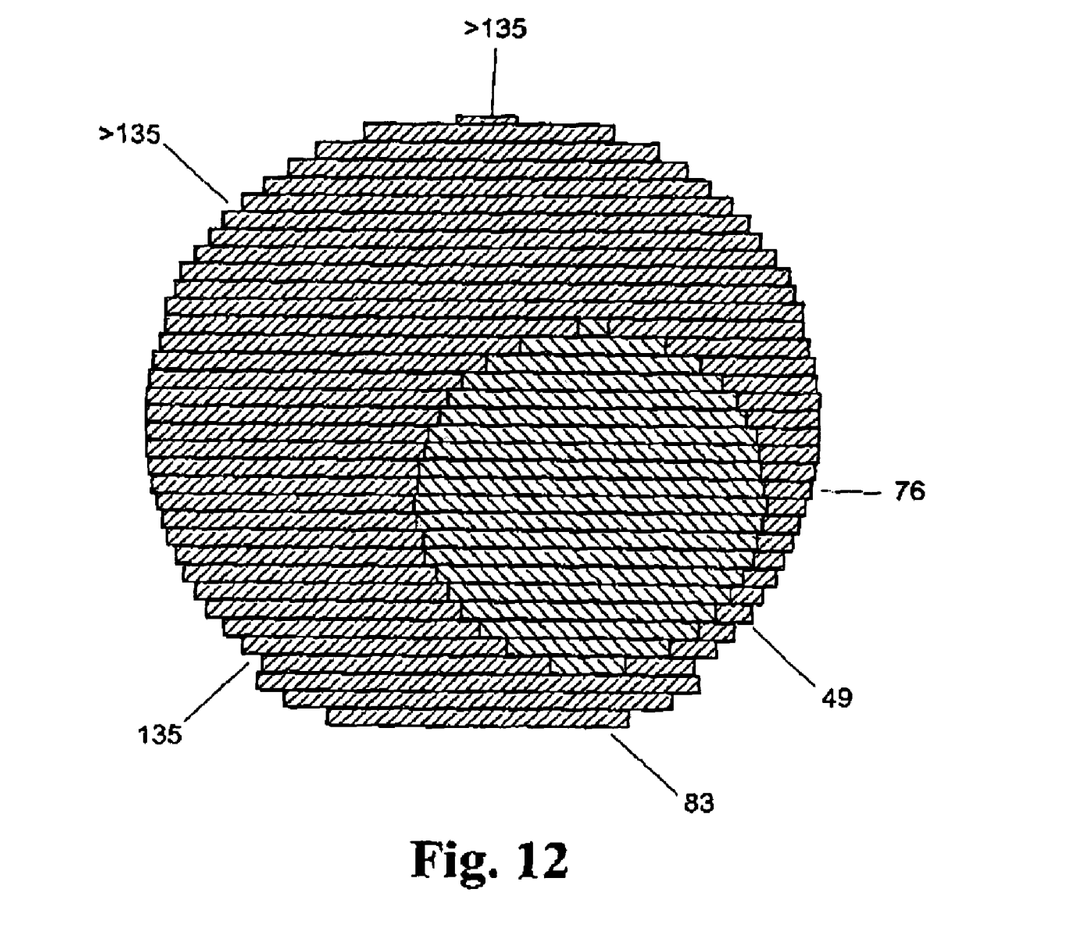
FIG. 12 is a backscatter profile of the wooden support of FIGS. 10 and 11.

An example of the use of transmission together with backscatter methodologies are provided in FIGS. 10 to 12.

An investigation of a wooden support 360 mm in diameter, with an internal hole of approximately 200 mm in diameter was conducted. Parameters used in the initial transmission methodology included density of 642.7 kg/m$^3$, scan diameter 376.98 mm, section modulus 5.0022×10$^6$ mm$^3$. FIG. 10 illustrates the results of initial transmission investigations in which an internal hole has been identified but the location not precisely resolved. FIG. 11 then illustrates the results of conducting an orthogonal scan to more accurately place the hole. FIG. 12 then illustrates the results of the backscatter scan in which actual dimensions have been measured, and are illustrated.

In this instance the limit of the dimensions which can be resolved via the backscatter technique is of the order of <100 mm i.e. when dimensions are >100 mm they are not accurately determinable. It should be noted that the orthogonal scanning step is optional and may indeed not be possible.

The foregoing describes the invention including preferred forms thereof. Alterations and modifications as will be obvious to those skilled in the art are intended to be incorporated in the scope hereof.

I claim:

1. A method of locating internal regions of unsound wood in a wooden support comprising the steps of:
    a) directing gamma rays approximately normal into the surface of the wooden support and detecting the gamma rays that are backscattered approximately 180 degrees; and
    b) comparing a detected backscatter rate with a backscatter rate or density of sound wood to estimate the thickness of sound wood.

2. A method as claimed in claims 1 herein steps a and b are carried out for a plurality of locations over the surface of the wooden support.

3. A method as claimed in claim 1 wherein the backscatter rate of sound wood is calculated using pre-calibration.

4. A method as claimed in claim 1 comprising, either before or after step a, determining the density of sound wood of the wooden support.

5. A method as claimed in claim 4 wherein the density of the sound wood is determined by directing gamma rays approximately normal into the surface of the wooden support in a region where there is at least 150 mm of sound wood, detecting the gamma rays that are backscattered approximately 180 degrees, and calculating the density.

6. A method as claimed in claim 1 comprising estimating the strength of the wooden support from the estimated thickness of sound wood.

7. A device for locating internal regions of unsound wood in a wooden support comprising: at least one gamma ray source for directing gamma rays approximately normal into the surface of the wooden support; at least one gamma ray detector for detecting the gamma rays that are backscattered approximately 180 degrees; and computation means arranged to receive a signal from the at least one detector, and to compare a detected backscatter rate with a backscatter rate or density of sound wood to estimate the thickness of sound wood.

8. A device as claimed in claim 7 wherein the computation means is arranged to estimate the strength of the wooden support.

9. A device as claimed in claim 7 wherein the gamma ray source(s) and gamma ray detectors(s) are positioned so that only those gamma rays that are Compton-scattered off atomic electrons through an angle close to 180 degrees are detected by the gamma ray detector(s).

10. A device as claimed in claim 7 which includes a transmitter or a memory device to store data produced by the gamma ray detector(s) in response to detected gamma rays.

11. A device as claimed in claim 7 wherein the apparatus includes a GPS unit.

* * * * *

UNITED STATES PATENT AND TRADEMARK OFFICE
CERTIFICATE OF CORRECTION

PATENT NO.        : 8,073,106 B2
APPLICATION NO.   : 12/804015
DATED             : December 6, 2011
INVENTOR(S)       : Gavin Wallace Page 1 of 1

It is certified that error appears in the above-identified patent and that said Letters Patent is hereby corrected as shown below:

Column 6, line 17 "they" should be --the y--.

Signed and Sealed this
Twentieth Day of March, 2012

David J. Kappos
*Director of the United States Patent and Trademark Office*